United States Patent
Wang et al.

(10) Patent No.: US 9,301,529 B2
(45) Date of Patent: Apr. 5, 2016

(54) POLYSUBSTITUTED PYRIDYL PYRAZOLECARBOXAMIDE AND PREPARATION METHOD AND USE THEREOF

(71) Applicant: ZHAOQING ZHENGE BIOLOGICAL TECHNOLOGY CO., LTD, Zhaoqing, Guangdong (CN)

(72) Inventors: Boli Wang, Zhaoqing (CN); Yong Zhao, Zhaoqing (CN); Daohang He, Zhaoqing (CN); Weiwen Li, Zhaoqing (CN)

(73) Assignee: ZHAOQING ZHENGE BIOLOGICAL TECHNOLOGY CO., LTD, Zhaoqing (CN)

( * ) Notice: Subject to any disclaimer, the term of this patent is extended or adjusted under 35 U.S.C. 154(b) by 0 days.

(21) Appl. No.: 14/621,422

(22) Filed: Feb. 13, 2015

(65) Prior Publication Data

US 2015/0322037 A1     Nov. 12, 2015

(30) Foreign Application Priority Data

May 7, 2014   (CN) .......................... 2014 1 0190515

(51) Int. Cl.
| | |
|---|---|
| C07D 401/04 | (2006.01) |
| A01N 43/56 | (2006.01) |
| C07D 413/14 | (2006.01) |
| C07C 221/00 | (2006.01) |
| C07C 253/14 | (2006.01) |
| C07C 227/16 | (2006.01) |

(52) U.S. Cl.
CPC .............. *A01N 43/56* (2013.01); *C07C 221/00* (2013.01); *C07C 227/16* (2013.01); *C07C 253/14* (2013.01); *C07D 401/04* (2013.01); *C07D 413/14* (2013.01)

(58) Field of Classification Search
CPC .................................................. C07D 401/04
USPC ........................................ 546/275.4; 514/341
See application file for complete search history.

(56) References Cited

U.S. PATENT DOCUMENTS

| | | | | |
|---|---|---|---|---|
| 8,153,844 B2* | 4/2012 | Davis | .................... | C07C 231/02 544/94 |
| 8,158,802 B2* | 4/2012 | Lahm | .................... | A01N 43/56 546/275.4 |
| 8,217,179 B2* | 7/2012 | Li | ........................ | C07D 401/04 546/275.4 |
| 8,492,409 B2* | 7/2013 | Li | ........................ | C07D 401/04 514/340 |
| 8,933,234 B2* | 1/2015 | Xu | ........................ | A01N 43/56 546/275.4 |

FOREIGN PATENT DOCUMENTS

| | | |
|---|---|---|
| CN | 1678192 A | 10/2005 |
| CN | 101333213 A | 12/2008 |
| CN | 102285966 A | 12/2011 |
| CN | 102391249 A | 3/2012 |
| WO | 2006068669 A1 | 6/2006 |
| WO | WO 2014/128188   * | 8/2014 |

OTHER PUBLICATIONS

Selby et al., "Discovery of, etc.," Bioorganic & Medicinal Chemistry Letters, 23 (2013) 6341-6345.*
Clark et al., "Synthesis of, etc.," Bioorganic & Medicinal Chemistry 16 (2008) 3163-3170.*
Liu et al. II, "Preparation of benzamide, etc.," CA 2008:134936.*

* cited by examiner

*Primary Examiner* — Patricia L Morris

(57) ABSTRACT

The present invention discloses a polysubstituted pyridyl pyrazolecarboxamide and its preparation method and use. The structure of the polysubstituted pyridyl pyrazolecarboxamide of the present invention is shown in the following General Formula I. The polysubstituted pyridyl pyrazolecarboxamide has the following advantages such as good insecticidal effect, low production cost; and it may be used in control of agriculture, forest or health pests, especially of resistant pests. For its preparation method, the yield is high, the number of steps is small, and the operation is simple.

6 Claims, No Drawings

POLYSUBSTITUTED PYRIDYL PYRAZOLECARBOXAMIDE AND PREPARATION METHOD AND USE THEREOF

CROSS-REFERENCE TO RELATED APPLICATION

This application claims the benefit of Chinese Patent Application No. 201410190515.2, filed on May 7, 2014, the contents of which are hereby incorporated by reference.

TECHNICAL FIELD

The present invention pertains to the technical field of pesticide preparation, specifically it relates to a polysubstituted pyridyl pyrazolecarboxamide and its preparation method and use.

BACKGROUND OF THE INVENTION

The hazards of frequent and extensive use of the conventional agrochemicals are of three aspects: the pests producing severe resistance; bringing about serious harm to the natural enemy creature of the pests; and causing pollution to the environment. Therefore, with the increasing enhancement of environmental protection consciousness of people, developing environment-friendly and new agrochemicals with high activity, high selectivity and low toxicity has become an urgent project of the pesticide science research, while it is also a trend of future agrochemicals development.

Prior to the present invention, in China Patent Application No. 02815924.1 Namul DuPont Company disclosed an arthropodicidal ortho-aminobenzamide compound, its structural formula is as shown in Formula i. PCT application No. PCT/US2005/026116 applied at Jul. 22, 2005 and titled "Mixtures of anthranilamide invertebrate pest control agents" discloses a compound having an excellent insecticidal activity as shown in Formula ii. China Patent Application No. 200810116198.4 titled "1-substituted pyridyl pyrazole carboxamides and its use" discloses compounds having insecticidal and bactericidal activity as shown in formula iii. China Patent Application No. 201110292614.8 titled "3,5-dichloropyridyl pyrazolecarboxamide compounds and use thereof" discloses compounds having excellent insecticidal activity and structure as shown in Formula iv. China Patent Application No. 201110292757.9 titled "3-fluoro-5-chloropyridyl pyrazolecarboxamides and use thereof" discloses compounds having insecticidal activity as shown in Formula V.

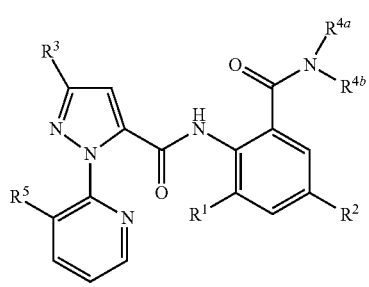

i

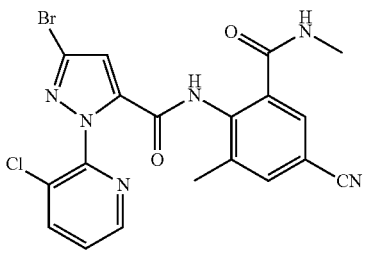

ii

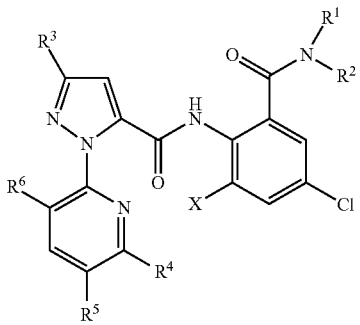

iii

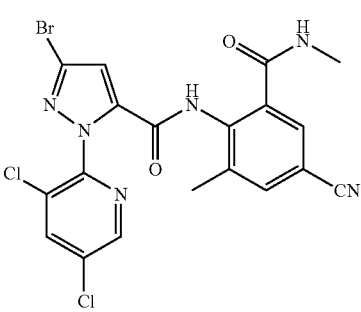

iv

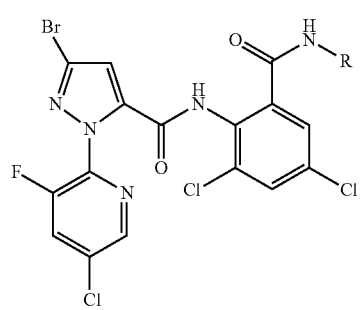

v

During practical use the above-described compounds have good control effect against the pests at a very low dose, however their production cost is high, severely restricting their extension and application.

SUMMARY OF THE INVENTION

The purpose of the present invention is to provide polysubstituted pyridyl pyrazolecarboxamides with good insecticidal activity and low production cost and preparation method thereof; such type of compounds can be used in control of agriculture, forest or health pests, especially in control of the resistant pests; for their preparation method, the yield was high, the number of steps is small, and the operation is simple.

In order to achieve above-described purpose, the structure of the polysubstituted pyridyl pyrazolecarboxamides of the present invention is as shown in General Formula I:

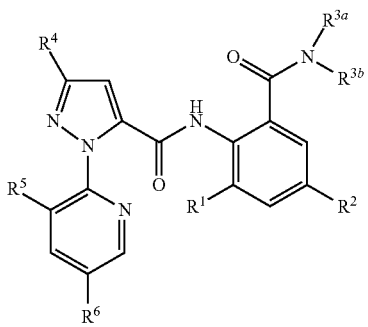

R¹ is Cl, Br or methyl;
R² is Cl, Br, I, CN or CF₃;
R$^{3a}$ is one of hydrogen or C₁-C₄ alkyl; R$^{3b}$ is H, amino, C₁-C₄ alkyl, C₃-C₆ alkenyl, C₃-C₆ cycloalkyl or, any hydrogen of the C₃-C₆ cycloalkyl is substituted by halogen, CN, amino, mercapto, hydroxyl, or multiple hydrogens are concurrently or respectively substituted by halogen, CN, amino, mercapto, hydroxyl;
Or R$^{3a}$ and R$^{3b}$ together with the linked nitrogen form one of

R⁴ is Br, CF₃ or CF₃CH₂O;
R⁵, R⁶ are concurrently or respectively H, F, Cl, Br, I, CN or CF₃.
The present invention also provides preparation methods of said polysubstituted pyridyl pyrazolecarboxamides, includes the following steps:
1) To an intermediate having a structural formula as shown in II of 1-(3,5-disubstituted pyridine-2-yl)-3-substituted-1H-pyrazole-5-carboxylic acid and 2-amino-3,5-disubstituted benzoic acid having a structural formula as shown in IV, a reaction solvent, alkali and appropriate amount of methanesulfonyl chloride are added, and reacted at −10 to 20° C. for 2 to 5 hours, to obtain an intermediate of 2-[1-(3,5-disubstituted-pyridine-2-yl)-3-substituted-1H-pyrazole-5-yl]-6,8-disubstituted-4H-3,1-benzoxazine-4-one having a structural formula as shown in V; and its reaction formula is:

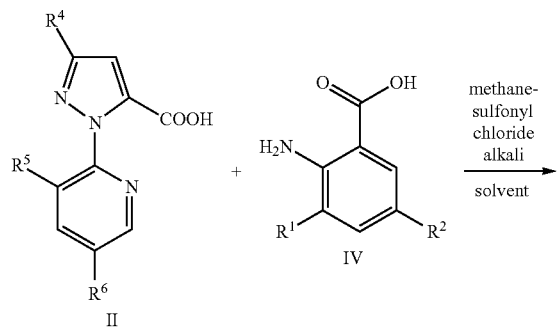

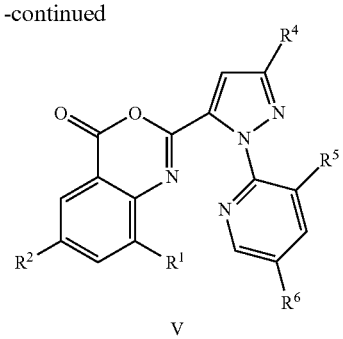

wherein, said extraction solvent is one of benzene, toluene, xylene, chlorobenzene, acetone, acetonitrile, ethyl acetate, tetrahydrofuran, dioxane; said alkali is one of sodium carbonate, potassium carbonate, sodium hydroxide, potassium hydroxide, triethylamine, pyridine, and methyl pyridine;
2) an intermediate having a structural formula as shown in V of benzoxazinone and a substituted primary amine or secondary amine having a structural formula as shown in VI are dissolved in an organic solvent, then reacted to form the polysubstituted pyridyl pyrazolecarboxamides having the structural formula as shown in I, and its reaction formula is:

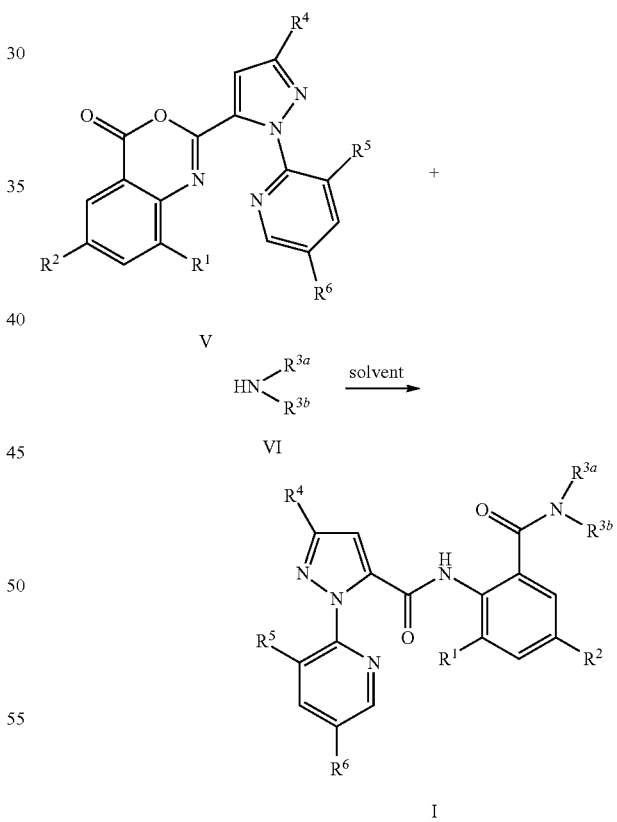

wherein, said organic solvent is one of acetone, acetonitrile, ethyl acetate, tetrahydrofuran, dioxane; said reaction temperature is 10 to 30° C., and the reaction time is 2 to 5 hours.
Preferably, the molar ratio of said intermediate having the structural formula of II and the intermediate having the structural formula of IV is 1:0.8 to 1.2; the molar ratio of the intermediate having the structural formula of II and alkali is 1:2.0 to 6.0; the molar ratio of the intermediate having the structural formula of II and methanesulfonyl chloride is 1:1.5 to 4.5; the molar ratio of benzoxazinones having the structural formula as shown in V and the substituted primary amine or secondary amine as shown in VI is 1:1.5 to 4.5.

More preferably, 2-amino-3,5-disubstituted benzoic acid having the structural formula as shown in IV is formed by reacting 2-amino-3-substituted benzoic acid having a structural formula as shown in VII with a halogenating or cyaniding reagent; and its reaction formula is:

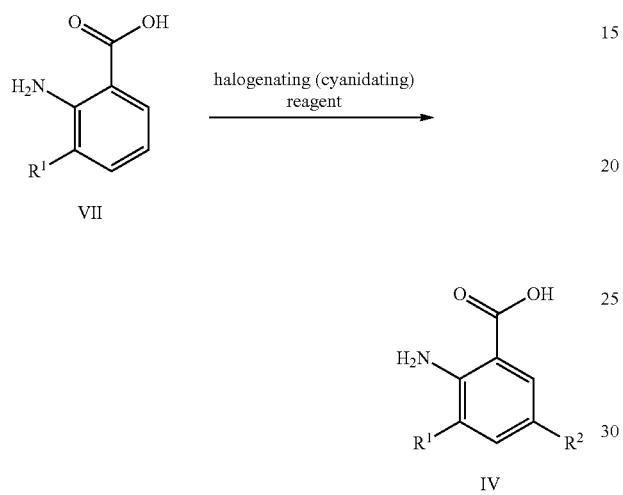

VII

IV wherein, said halogenating or cyaniding reagent is one of N-chlorosuccinimide, N-bromosuccinimide, N-iodosuccinimide, chlorine gas, bromine, iodine, iodine monochloride, sodium cyanide, cuprous cyanide, zinc cyanide; and the reaction temperature is 40 to 150° C.; the reaction time is 2 to 6 hours; the molar ratio of 2-amino-3-substituted benzoic acid having the structural formula as shown in IV and said halogenating or cyaniding reagent is 1:0.8 to 1.3.

The present invention also provides another preparation method of said polysubstituted pyridyl pyrazolecarboxamide, it is formed by reacting the intermediate of 1-(3,5-disubstituted pyridine-2-yl)-3-substituted-1H-pyrazole-5-carboxylic acid having the structural formula shown in II and an intermediate of 2-amino-3,5-disubstituted benzamide having a structural formula as shown in III with alkali and methanesulfonyl chloride in a solvent containing a catalyst; and its reaction formula is:

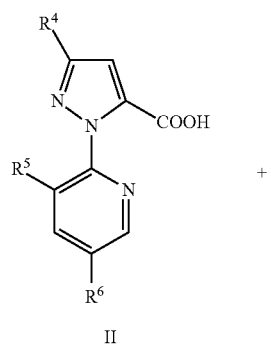

II

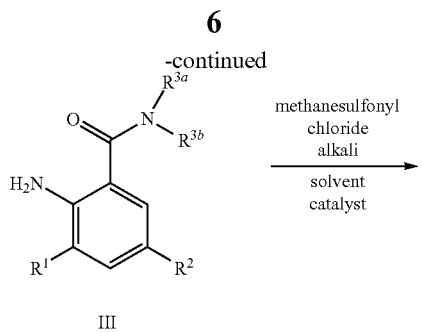

III

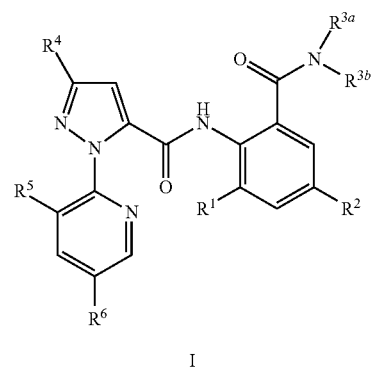

I wherein, said catalyst is one of potassium iodide, sodium iodide; said solvent is one of benzene, toluene, xylene, chlorobenzene, acetone, acetonitrile, ethyl acetate, tetrahydrofuran, dioxane; said alkali is one of sodium carbonate, potassium carbonate, sodium hydroxide, potassium hydroxide, triethylamine, pyridine, methyl pyridine;

Preferably, the molar ratio of said intermediate having the structural formula as shown in II and the intermediate having the structural formula as shown in III is 1:0.8 to 1.2; the molar ratio of the intermediate having the structural formula as shown in II and the alkali is 1:2.0 to 6.0; the molar ratio of the intermediate having the structural formula as shown in II and methanesulfonyl chloride is 1:1.5-4.5; said reaction temperature is −10 to 25° C., and the reaction time is 0.5 to 1.5 hours.

Further, the intermediate of 2-amino-3,5-disubstituted benzamide having the structural formula as shown in III is formed by conducting a methylation reaction to the intermediate having the structural formula as shown in IV of 2-amino-3,5-disubstituted benzoic acid, generating an intermediate having a structural formula as shown in VIII of 2-amino-3,5-disubstituted benzoic acid methyl ester, then conducting an amination reaction with the substituted primary amine or secondary amine having the structural formula as shown in VI; and its reaction formula is:

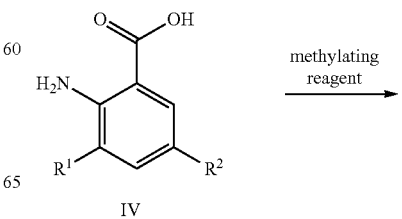

IV

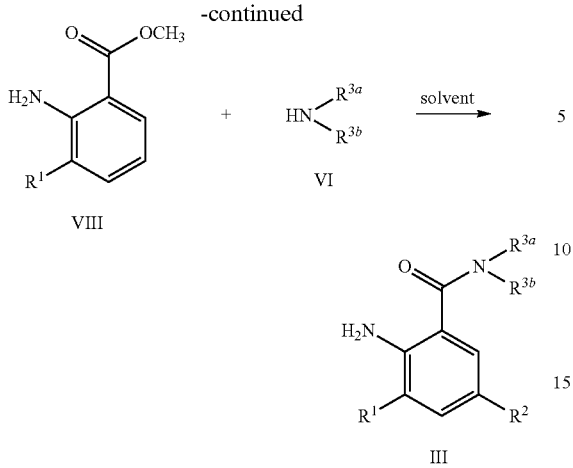

wherein, said methylating reagent is one of sulfuric acid/ methanol, potassium carbonate/dimethyl sulfate, potassium carbonate/methyl iodide, and the methylation reaction temperature is 20 to 110° C.;

the temperature of said amination reaction is 50 to 70° C., the solvent of the amination is one of methanol, ethanol, acetonitrile, tetrahydrofuran; the molar ratio of said intermediate having the structural formula as shown in VIII of 2-amino-3,5-disubstituted benzoic acid methyl ester and the substituted primary amine or secondary amine having the structural formula as shown in VI is 1:3.5 to 5.0.

The present invention also provides a use of said polysubstituted pyridyl pyrazolecarboxamides as insecticide.

An insecticide, the weight percentage of said polysubstituted pyridyl pyrazole carboxamide is 1 to 99%. The insecticide may be used in control of agriculture, forest or health pests, and arthropod such as harmful mite, especially in control of the resistant pests, and harmful mites; there are no cross-resistance with the existing conventional insecticides, furthermore it has the following characteristics such as low toxicity, being environment-friendly, safe to use, broad-spectrum and long persistence. It is an arthropodicidal active substance having an extensive application prospect.

DETAILED DESCRIPTION OF THE INVENTION

Hereinafter, the polysubstituted pyridyl pyrazolecarboxamides and preparation method and use thereof according to the present invention will be described in more detail in conjunction with the specific examples.

The structural formulae and the properties of some of the representative compounds of polysubstituted pyridyl pyrazolecarboxamides of the present invention are as shown in Table 1:

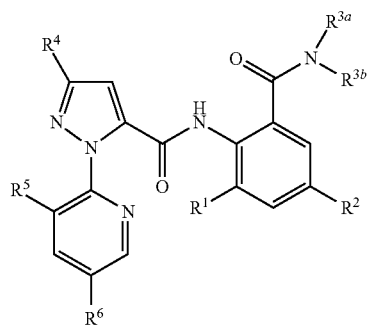

TABLE 1 the structures and the properties of some of the compounds

| Compound | $R^1$ | $R^2$ | $R^{3a}$ | $R^{3b}$ | $R^4$ | $R^5$ | $R^6$ | m.p.(° C.) |
|---|---|---|---|---|---|---|---|---|
| I-1 | $CH_3$ | I | $CH_3CH_2$ | $CH_3CH_2$ | Br | Cl | H | 198.4-199.1 |
| I-2 | $CH_3$ | I | $CH(CH_3)_2$ | $CH(CH_3)_2$ | Br | Cl | H | 189.2-189.9 |
| I-3 | $CH_3$ | I | H | $C(CH_3)_3$ | Br | Cl | H | 199.0-200.2 |
| I-4 | $CH_3$ | Cl | H | $CH_2CH_2OH$ | Br | Cl | H | 211.7-213.2 |
| I-5 | $CH_3$ | Cl | H | $CH_2CH_2NEt_2$ | Br | Cl | H | 201.8-202.4 |
| I-6 | $CH_3$ | Cl | H | $CH_2CF_3$ | Br | Cl | H | 211.5-213.6 |
| I-7 | $CH_3$ | Cl | H | cyclopropyl-C(CH₃)- | Br | Cl | H | 201.7-203.2 |
| I-8 | $CH_3$ | Cl | H | $H_2CH_2C$-C₆H₄-F | Br | Cl | H | 179.2-181.5 |
| I-9 | $CH_3$ | Cl | H | $H_2CH_2C$-C₆H₃(OCH₃)₂ | Br | Cl | H | 165.1-166.4 |
| I-10 | $CH_3$ | Br | H | $CH_3$ | Br | Cl | H | 230.1-231.0 |
| I-11 | $CH_3$ | Br | H | $CH_3CH_2$ | Br | Cl | H | 185.0-186.4 |
| I-12 | $CH_3$ | Br | H | cyclopropyl-C(CH₃)- | Br | Cl | H | 213.2-214.4 |

TABLE 1-continued the structures and the properties of some of the compounds

| Compound | $R^1$ | $R^2$ | $R^{3a}$ | $R^{3b}$ | $R^4$ | $R^5$ | $R^6$ | m.p.(° C.) |
|---|---|---|---|---|---|---|---|---|
| I-13 | $CH_3$ | Br | H | $C(CH_3)_3$ | Br | Cl | H | 229.0-230.3 |
| I-14 | $CH_3$ | I | H | $CH_3$ | Br | Cl | H | 201.7-202.2 |
| I-15 | $CH_3$ | I | H | $CH_3CH_2$ | Br | Cl | H | 181.1-182.7 |
| I-16 | $CH_3$ | I | H | cyclopropylmethyl | Br | Cl | H | 246.5-247.2 |
| I-17 | $CH_3$ | CN | H | $CH_3$ | Br | Cl | H | 165.3-166.5 |
| I-18 | $CH_3$ | CN | H | $CH_3CH_2$ | Br | Cl | H | 207.9-209.1 |
| I-19 | $CH_3$ | CN | H | cyclopropylmethyl | Br | Cl | H | 231.2-233.1 |
| I-20 | $CH_3$ | CN | H | $C(CH_3)_3$ | Br | Cl | H | 245.8-247.2 |
| I-21 | $CH_3$ | Cl | H | $CH_3$ | Br | Cl | H | 192.2-193.9 |
| I-22 | $CH_3$ | Cl | H | $CH_3CH_2$ | Br | Cl | H | 209.1-211.3 |
| I-23 | $CH_3$ | Cl | H | cyclopropylmethyl | Br | Cl | H | 220.6-222.2 |
| I-24 | $CH_3$ | Cl | H | $C(CH_3)_3$ | Br | Cl | H | 219.3-220.9 |
| I-25 | $CH_3$ | Cl | H | $CH_2CH_2OH$ | Br | F | Cl | 233.7-234.5 |
| I-26 | $CH_3$ | Cl | H | $CH_2CH_2NEt_2$ | Br | F | Cl | 220.8-221.1 |
| I-27 | $CH_3$ | Br | H | $CH_2CH_2OH$ | Br | F | Cl | 239.4-241.1 |
| I-28 | $CH_3$ | Br | H | $CH_2CH_2NEt_2$ | Br | F | Cl | 219.8-221.3 |
| I-29 | $CH_3$ | Cl | H | $CH_2CH_2OH$ | Br | Cl | H | 236.9-238.1 |
| I-30 | $CH_3$ | Cl | H | $CH_2CH_2NEt_2$ | Br | Cl | Cl | 233.6-234.3 |
| I-31 | $CH_3$ | Br | H | $CH_2CH_2OH$ | Br | Cl | Cl | 202.7-204.0 |
| I-32 | $CH_3$ | Br | H | $CH_2CH_2NEt_2$ | Br | Cl | Cl | 193.4-194.6 |

Example 2

The preparation of the compound of I-1 in Example 1, its reaction formula is:

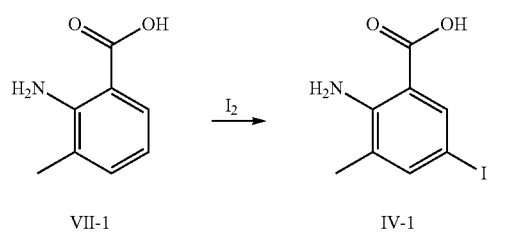

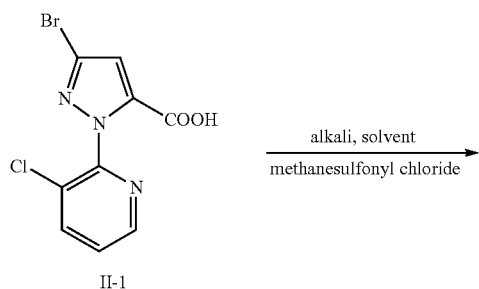

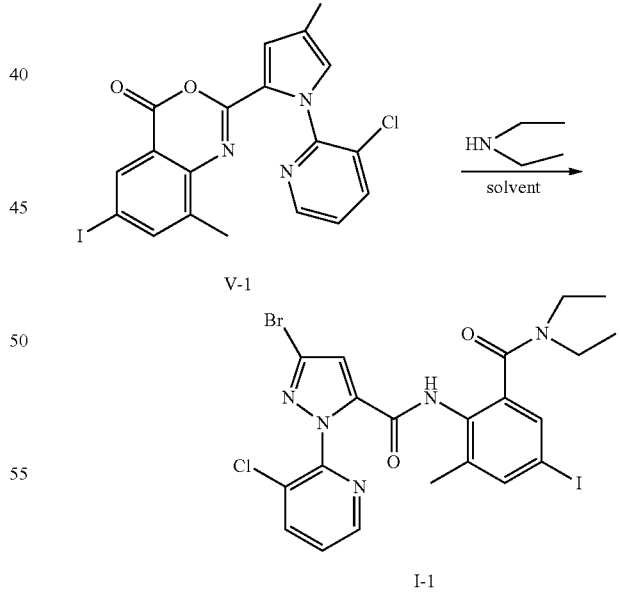

Its preparation method includes the following steps:

To a 50 mL round-bottom flask, 16.5 mmol of 2-amino-3-methylbenzoic acid having the structural formula as shown in VII-1, 20 mL of carbon tetrachloride, 20 mmol of iodine and 0.3 gram of potassium persulfate were added, heated to 77° C. and reacted for 6 hours, cooled to room temperature and 50 mL of saturated sodium bisulfite solution was added, stirred for 15 minutes, a large amount of solid was precipitated, filtered and dried to obtain 4.47 grams of the intermediate having the structural formula as shown in IV-1 of 2-amino-3-methyl-5-iodo-benzoic acid, and the yield was 97.7%;

To a 50 mL round-bottom flask, 6.0 mmol of 2-amino-3-methyl-5-iodobenzoic acid having a structural formula as shown in IV-1, 6.0 mmol of 1-(3-chloropyridine-2-yl)-3-bromo-1H-pyrazole-5-carboxylic acid having a structure as shown in Formula II-1, and 20 mL of acetonitrile were added, 24 mmol of methylpyridine was dripped, cooled to −8° C., 5 mL of acetonitrile solution of 12 mmol methanesulfonyl chloride was dripped, after dripping was completed, stirred at −2° C. for 0.5 hour, stirred at 15° C. for 3 hours, 15 mL of water was added and stirred for 20 minutes, filtered, washed with 20 mL of water twice, dried to obtain 2.67 grams of the intermediate having a structure as shown in Formula V-1 of 2-[1-(3-chloropyridine-2-yl)-3-bromo-1H-pyrazole-5-yl]-6-iodo-8-methyl-4H-3,1-benzoxazine-4-one, and the yield was 98.5%;

To a 50 mL round-bottom flask, 3.0 mmol of benzoxazinone having the structure as shown in Formula V-1, 15 mL of acetonitrile, 9.0 mmol of diethylamine were added, heated to 25 to 30° C. and reacted for 2.0 hours, 10 mL of water was added and stirred for 0.5 hour, filtered and dried to obtain 1.73 grams of 1-(3-chloropyridine-2-yl)-3-bromo-N-(2-methyl-4-iodo-6-diethylaminocarbonyl)phenyl-1H-pyrazole-5-formamide having the structural formula as shown in I-1 as a white solid, and the yield was 93.5%.

Example 3

The preparation of the compound of I-3 in Example 1, its reaction formula is:

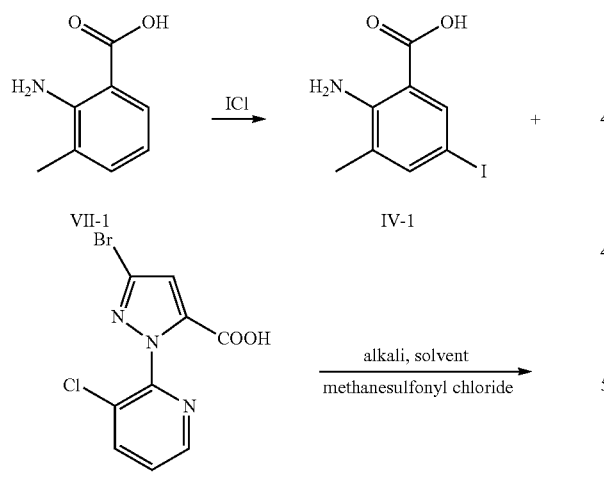

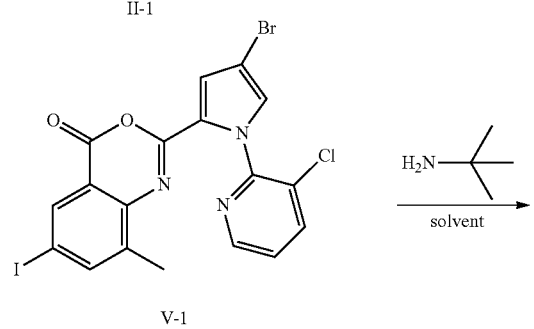

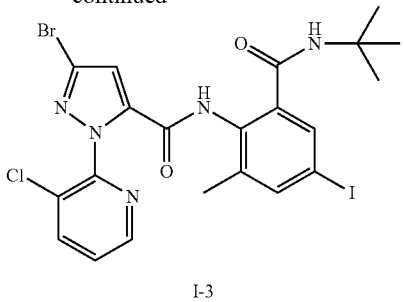

I-3

Its production method includes the following steps:

To a 50 mL round-bottom flask, 16.5 mmol of 2-amino-3-methylbenzoic acid having the structural formula as shown in VII-1, 10 mL of iodine monochloride were added, heated to 80° C. and reacted for 6 hours, washed with 5% hydrochloric acid, after a conventional treatment 4.35 grams of 2-amino-3-methyl-5-iodo-benzoic acid having a structural formula as shown in IV-1 was obtained, and the yield was 95.5%;

To a 50 mL round-bottom flask, 6.0 mmol of 2-amino-3-methyl-5-iodo-benzoic acid having the structural formula of IV-1, 6.0 mmol of 1-(3-chloropyridine-2-yl)-3-bromo-1H-pyrazole-5-carboxylic acid having a structure formula of II-1, and 20 mL of tetrahydrofuran were added, 24 mmol of triethylamine was dripped, cooled to −8° C. and 5 mL of tetrahydrofuran solution of 12 mmol of methanesulfonyl chloride was dripped, after dripping was completed, stirred at −2° C. for 0.5 hour, stirred at 15° C. for 3 hours, then 15 mL of water was added and stirred for 20 minutes, filtered, washed with 20 mL of water twice, dried to obtain 2.71 grams of the intermediate having the structure as shown in formula V-1 of 2-[1-(3-chloropyridine-2-yl)-3-bromo-1H-pyrazole-5-yl]-6-iodo-8-methyl-4H-3,1-benzoxazine-4-one, and the yield was 98.9%;

To a 50 mL round-bottom flask, 3.0 mmol of benzoxazinone having the structure as shown in formula V-1, 15 mL of tetrahydrofuran, 9.0 mmol of tert-butylamine were added, heated to 25 to 27° C. and reacted for 2.0 hours, then 10 mL of water was added and stirred for 0.5 hour, filtered, dried to obtain 1.76 grams of 1-(3-chloropyridine-2-yl)-3-bromo-N-(2-methyl-4-iodo-6-tert-butylaminocarbonyl)phenyl-1H-pyrazole-5-formamide having a structural formula of I-3 as a white solid, and the yield was 95.5%.

Example 4

Preparation of the compound of I-18 in Example 1, its reaction formula is:

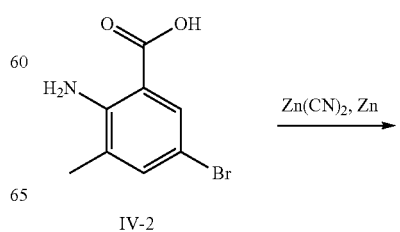

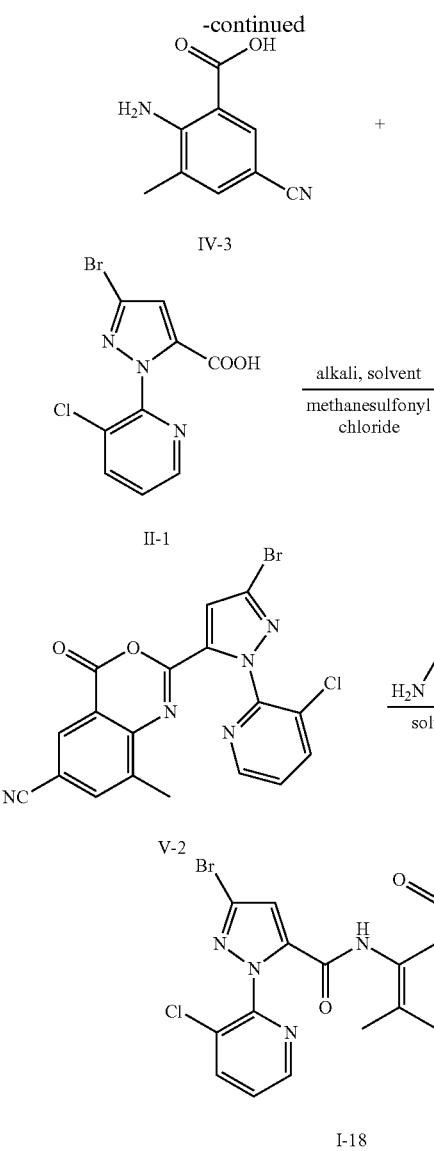

of an intermediate of 2-[1-(3-chloropyridine-2-yl)-3-bromo-1H-pyrazole-5-yl]-6-cyano-8-methyl-4H-3,1-benzoxazine-4-one having the structural formula as shown in V-2, and the yield was 92.4%;

To a 50 mL round-bottom flask, 3.0 mmol of benzoxazinone, 15 mL of acetone, 9.0 mmol of ethylamine were added, heated to 25 to 27° C. and reacted for 1.0 hour, then 10 mL of water was added and stirred for 0.5 hour, filtered and dried to obtain 1.33 grams of 1-(3-chloropyridine-2-yl)-3-bromo-N-(2-methyl-4-cyano-6-ethylaminocarbonyl)phenyl-1H-pyrazole-5-formamide having a structural formula as shown in I-18 as a white solid, and the yield was 91.1%.

Example 5

The preparation of compound of I-24 in Example 1, its reaction formula was:

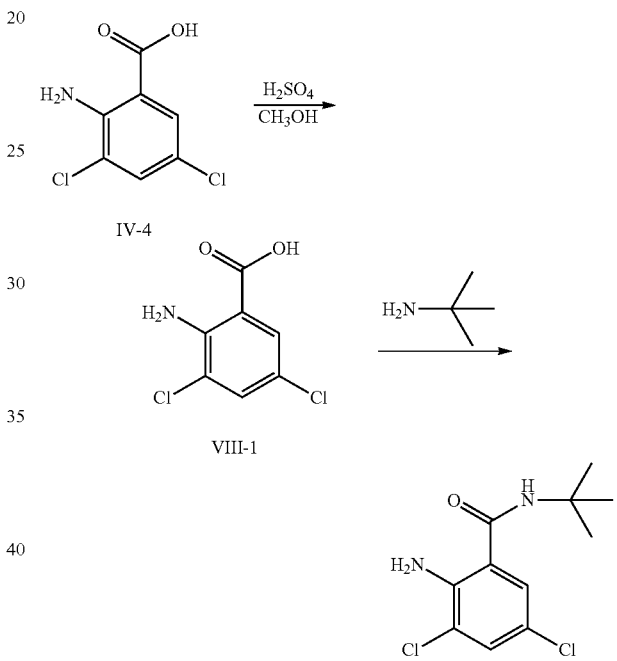

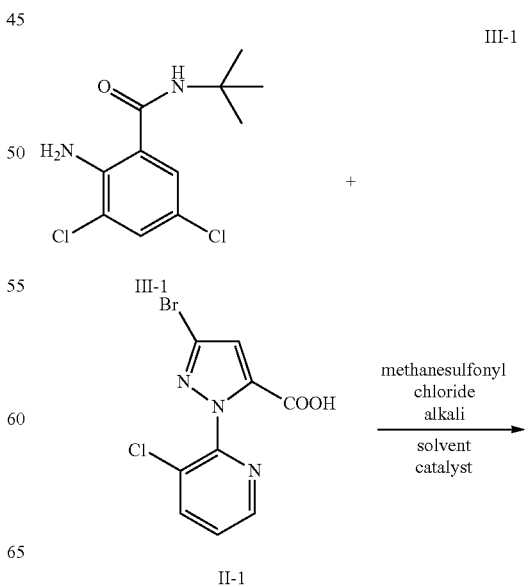

Its preparation method includes the following steps:

To a 50 mL round-bottom flask, 10.0 mmol of 2-amino-3-methyl-5-bromobenzoic acid having the structural formula as shown in IV-2, 10 mL of 1,4-dioxane and 12.0 mmol of zinc cyanide and 0.5 gram of activated zinc powder were added, heated to 125° C. under protection by nitrogen gas and reacted for 12 hours, filtered and the solvent was removed under reduced pressure, after a conventional treatment 1.35 grams of 2-amino-3-methyl-5-cyanobenzoic acid having a structural formula as shown in IV-3 was obtained, and the yield was 76.7%;

To a 50 mL round-bottom flask, 6.0 mmol of 2-amino-3-methyl-5-cyanobenzoic acid having the structural formula as shown in IV-3, 6.0 mmol of 1-(3-chloropyridine-2-yl)-3-bromo-1H-pyrazole-5-carboxylic acid having the structural formula as shown in II-1, and 20 mL of acetonitrile were added, 24 mmol of pyridine was dripped, cooled to −8° C. and 5 mL of acetonitrile solution of 12 mmol methanesulfonyl chloride was dripped, after the dripping was completed, stirred at −2° C. for 0.5 hour, stirred at 15° C. for 3 hours, then 15 mL of water was added and stirred for 20 minutes, filtered, washed with 20 mL of water twice, dried to obtain 2.45 grams

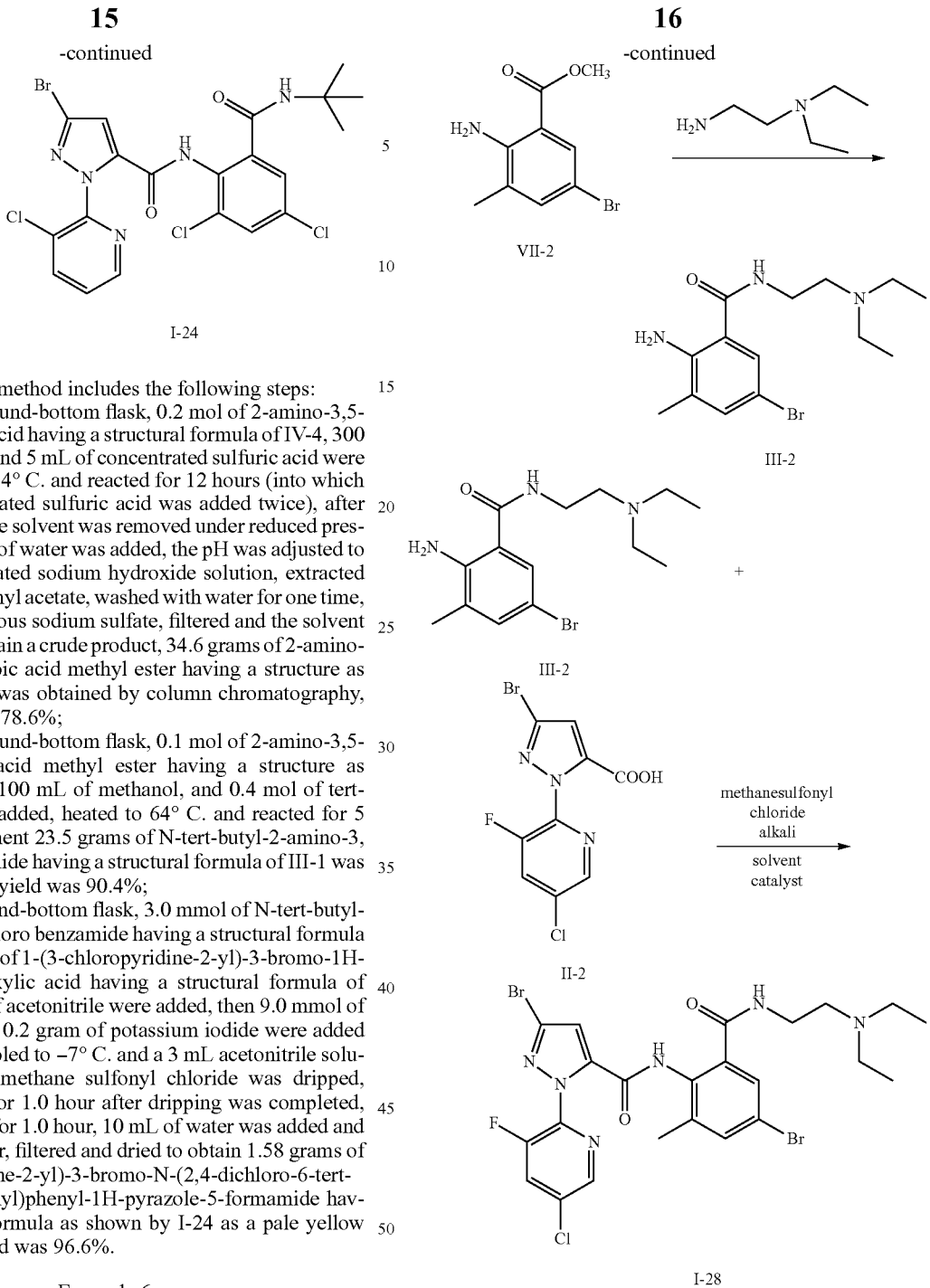

Its preparation method includes the following steps:

To a 500 mL round-bottom flask, 0.2 mol of 2-amino-3,5-dichlorobenzoic acid having a structural formula of IV-4, 300 mL of methanol, and 5 mL of concentrated sulfuric acid were added, heated to 64° C. and reacted for 12 hours (into which 3 mL of concentrated sulfuric acid was added twice), after cooling most of the solvent was removed under reduced pressure, and 300 mL of water was added, the pH was adjusted to 9-10 with a saturated sodium hydroxide solution, extracted with 200 mL of ethyl acetate, washed with water for one time, dried over anhydrous sodium sulfate, filtered and the solvent was remove to obtain a crude product, 34.6 grams of 2-amino-3,5-dichlorobenzoic acid methyl ester having a structure as shown by VIII-1 was obtained by column chromatography, and the yield was 78.6%;

To a 100 mL round-bottom flask, 0.1 mol of 2-amino-3,5-dichlorobenzoic acid methyl ester having a structure as shown in VIII-1, 100 mL of methanol, and 0.4 mol of tert-butylamine were added, heated to 64° C. and reacted for 5 hours, after treatment 23.5 grams of N-tert-butyl-2-amino-3,5-dichlorobenzamide having a structural formula of III-1 was obtained, and the yield was 90.4%;

To a 50 mL round-bottom flask, 3.0 mmol of N-tert-butyl-2-amino-3,5-dichloro benzamide having a structural formula of III-1, 3.0 mmol of 1-(3-chloropyridine-2-yl)-3-bromo-1H-pyrazole-5-carboxylic acid having a structural formula of II-1, and 10 mL of acetonitrile were added, then 9.0 mmol of triethylamine and 0.2 gram of potassium iodide were added under stirring, cooled to −7° C. and a 3 mL acetonitrile solution of 9 mmol methane sulfonyl chloride was dripped, reacted at 0° C. for 1.0 hour after dripping was completed, reacted at 20° C. for 1.0 hour, 10 mL of water was added and stirred for 0.5 hour, filtered and dried to obtain 1.58 grams of 1-(3-chloropyridine-2-yl)-3-bromo-N-(2,4-dichloro-6-tert-butylaminocarbonyl)phenyl-1H-pyrazole-5-formamide having a structural formula as shown by I-24 as a pale yellow solid, and the yield was 96.6%.

Example 6

The preparation of the compound of I-28 in Example 1, its reaction formula is:

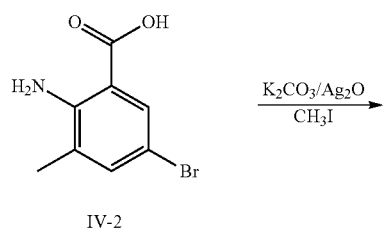

Its preparation method includes the following steps:

To a 500 mL round-bottom flask, 0.2 mol of 2-amino-3-methyl-5-bromobenzoic acid having the structural formula of IV-2, 200 mL of acetone, 2 grams of potassium carbonate and 0.5 gram of silver oxide were added, stirred at room temperature for 0.5 hour, 0.3 mmol of methyl iodide was dripped, and reacted at a temperature range of 20-30° C. for 18 hours, filtered to remove the solid, washed with water, extracted with dichloromethane, dried over anhydrous sodium sulfate, the solvent was removed to obtain 45.3 grams of an intermediate of 2-amino-3-methyl 5-bromobenzoic acid methyl ester having a structural formula of VIII-2, and the yield was 92.8%;

To a 100 mL round-bottom flask, 0.1 mol of 2-amino-3-methyl 5-bromobenzoic acid methyl ester having the structural formula of VIII-2, 100 mL of ethanol, 0.3 mol of N,N-diethyl ethylenediamine were added, heated to 78° C. and reacted for 4 hours, after treatment 27.5 grams of N-diethylaminoethyl-2-amino-3-methyl-5-bromobenzamide having a structural formula of III-2 was obtained, and the yield was 84.2%;

To a 50 mL round-bottom flask, 3.0 mmol of N-diethylaminoethyl-2-amino-3-methyl-5-bromobenzamide having the structural formula of III-2, 3.0 mmol of 1-(3-fluoro-5-chloropyridine-2-yl)-3-bromo-1H-pyrazole-5-carboxylic acid having a structural formula of II-2, 10 mL of tetrahydrofuran, and 9.0 mmol of methyl pyridine and 0.2 gram of sodium iodide were added under stirring, cooled to −5° C., a 3 mL of tetrahydrofuran solution of 12 mmol methanesulfonyl chloride was dripped, reacted at 0° C. for 1.0 hour after dripping was completed, and reacted at 20° C. for 1.0 hour, 10 mL of water was added and stirred for 0.5 hour, filtered and dried to obtain 1.73 grams of 1-(3-fluoro-5-chloropyridine-2-yl)-3-bromo-N-(2-methyl-4-bromo-6-diethylamino ethylaminocarbonyl)phenyl-1H-pyrazole-5-formamide having a structural formula as shown in I-28 as a white solid, and the yield was 91.5%.

Example 7

The preparation of the compound of I-29 in Example 1, its reaction formula is:

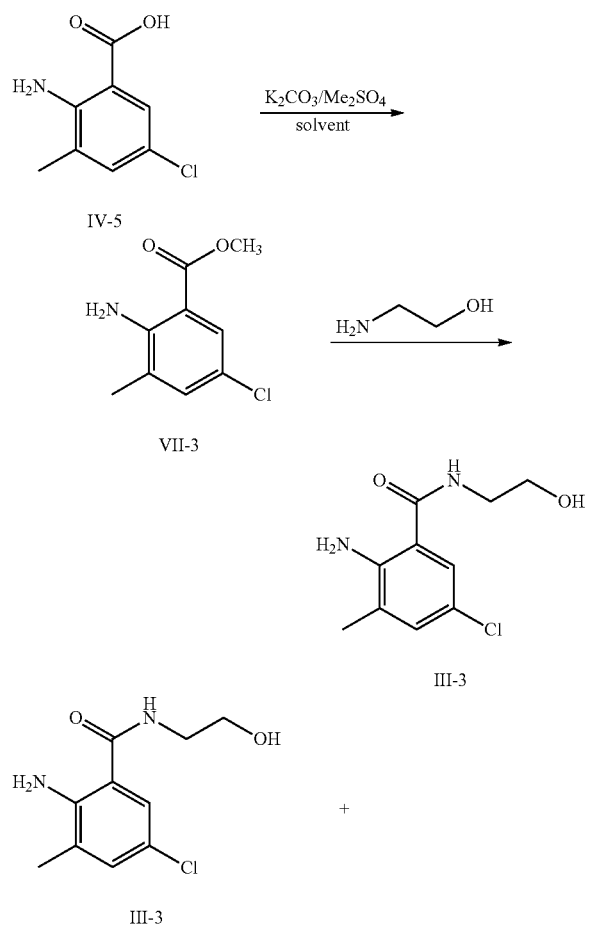

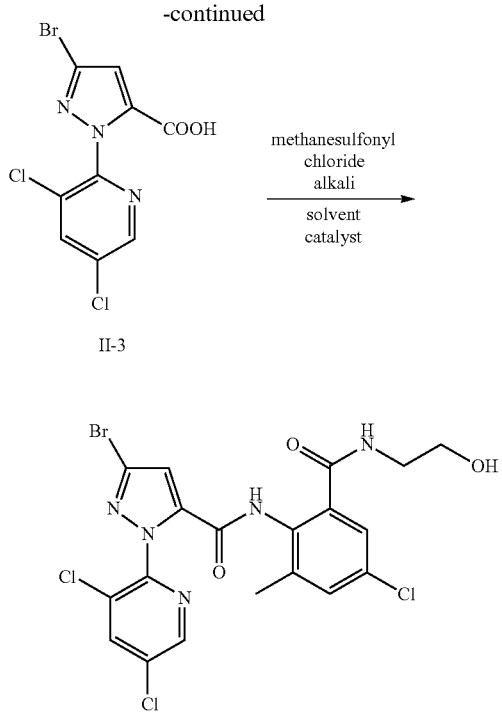

Its preparation method includes the following steps:

To a 500 mL round-bottom flask, 0.2 mol of 2-amino-3-methyl-5-chlorobenzoic acid having the structural formula of IV-5, 300 mL of DMF and 2.0 grams of potassium carbonate were added, stirred at room temperature for 0.5 hour, dimethyl sulfate was dripped, reacted at 110° C. for 7 hours, and cooled to room temperature, poured into a saturated sodium chloride solution, extracted with acetate ethyl, dried over anhydrous sodium sulfate, filtered and the solvent was removed to obtain a crude product, 35.2 grams of 2-amino-3-methyl-5-chlorobenzoic acid methyl ester having a structural formula of VIII-3 was obtained by column chromatography, and the yield was 88.4%;

To a 100 mL round-bottom flask, 0.1 mol of 2-amino-3-methyl-5-chlorobenzoic acid methyl ester having the structural formula of VIII-3, 100 mL of acetonitrile, 0.4 mol of ethanolamine were added, heated to 70° C. and reacted for 3 hours, after treatment 20.2 grams of N-hydroxyethyl-2-amino-3-methyl-5-chlorobenzamide having a structural formula of III-3 was obtained, and the yield was 88.4%; To a 50 mL round-bottom flask, 3.0 mmol of N-hydroxyethyl-2-amino-3-methyl-5-chlorobenzamide having the structural formula of III-3, 3.0 mmol of 1-(3,5-dichloropyridine-2-yl)-3-bromo-1H-pyrazole-5-carboxylic acid having a structural formula of II-3, 10 mL of acetonitrile were added, and 9.0 mmol of potassium carbonate and 0.2 gram of potassium iodide were added under stirring, cooled to −7° C. and a 3 mL acetonitrile solution of 12 mmol methanesulfonyl chloride was dripped, after dripping was completed reacted at 0° C. for 1.0 hour, reacted at 20° C. for 1.0 hour, 10 mL of water was added and stirred for 0.5 hour, filtered and dried to obtain 1.52 grams of 1-(3,5-dichloropyridine-2-yl)-3-bromo-N-(2-methyl-4-chloro-6-hydroxyethylaminocarbonyl)phenyl-1H-pyrazole-5-formamide having a structural formula of I-29 as a pale yellow solid, and the yield was 92.7%.

Example 8

Bioactivity Determination

Determination of Activity Against *Helicoverpa armigera*

Leaf dipping method (proposed by Insecticide Resistance Action Committee, IRAC) was adopted: a leaf of *Brassica oleracea* was clamped by a tweezer and dipped into an insecticide solution having a certain concentration to be tested for 3 to 5 seconds, the excessive solution was threw off, one leaf at each time, three leaves for each sample. The leaves were placed onto a treatment paper according to sequence of sample marking and air-dried naturally, then put into a marked straight tube of 10 cm length, and 30 *Plutella xylostella* larvae being 2 year-old were placed in, the tube opening was covered by a gauze, and placed into a standard treatment chamber, the result was checked and the mortality was calculated at 72 hour.

Determination of Activity Against *Ostrinia furnacalis*

Leaf dipping method was adopted, a leaf of *Brassica oleracea* was clamped by a tweezer, and dipped in insecticide solution having a certain concentration for 3 to 5 seconds, the excessive solution was threw off, one leaf at each time, and three leaves for each sample. The leaves were placed onto a treatment paper according to the sequence of sample marking and air-dried naturally, then put into a marked straight tube of 10 cm length, and 30 *Ostrinia furnacalis* larvae being 3 year-old were place in, the tube opening was covered by a gauze, and placed in a standard treatment chamber, the result was checked and the mortality was calculated at 72 hours.

Some of the compounds in Example 1 were used to conduct the test, and a control compound was selected to conduct an indoor insecticidal activity data (%, concentration unit: ppm) determination test under the same condition, the results of the test was shown in Table 2.

The structural formula of the control compound KC (a compound described in China Patent Application No. 02815924.1 of DuPont company, Chinese Name: 氯虫酰胺, trade name: 康宽) was:

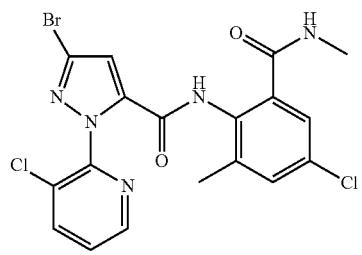 [SMILES: CNC(=O)c1cc(Cl)cc(C)c1NC(=O)c1cc(Br)nn1-c1ncccc1Cl]

TABLE 2

| Compound | Target | Concentrattion | | | | | |
|---|---|---|---|---|---|---|---|
| | | 0.5 ppm | 0.25 ppm | 0.125 ppm | 0.0625 ppm | 0.031 ppm | 0.016 ppm |
| I-5 | *Helicoverpa armigera* | 100 | 100 | 100 | 100 | 70 | 50 |
| | *Ostrinia furnacalis* | 100 | 100 | 100 | 100 | 100 | 80 |
| I-13 | *Helicoverpa armigera* | 100 | 100 | 100 | 80 | 65 | 30 |
| | *Ostrinia furnacalis* | 100 | 100 | 100 | 100 | 85 | 50 |
| I-24 | *Helicoverpa armigera* | 100 | 100 | 100 | 100 | 80 | 60 |
| | *Ostrinia furnacalis* | 100 | 100 | 100 | 100 | 100 | 85 |
| KC | *Helicoverpa armigera* | 85 | 70 | 55 | 30 | 0 | 0 |
| | *Ostrinia furnacalis* | 100 | 100 | 75 | 55 | 30 | 0 |

The data in Table 2 indicate that the control effect against *Helicoverpa armigera* by some of the tested compounds were quite remarkable at a concentration as low as 0.125 ppm, and the mortality reached 100%, and the mortality of *Helicoverpa armigera* at 0.031 ppm was above 65%; the control effect against *Ostrinia furnacalis* were particularly remarkable, the mortality of *Ostrinia furnacalis* to I-13 and I-24 was 100% at 0.031 ppm, the inhibitory activity was above 80% even at 0.016 ppm.

The data also indicate that at same concentration, the control effect against *Helicoverpa armigera* and *Ostrinia furnacalis* some by the tested compounds was superior to the control compound KC.

What is claimed is:

1. A compound having the following structure:

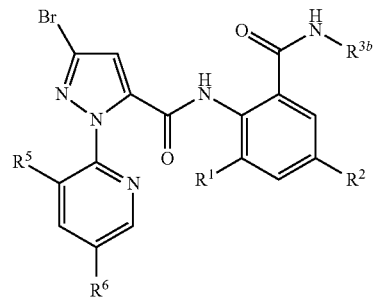

wherein,
$R^1$ is methyl;
$R^2$ is Cl or Br;
$R^{3b}$ is —$CH_2CH_2OH$ or —$CH_2CH_2N(CH_2CH_3)_2$;
$R^5$ is Cl or F;
$R^6$ is hydrogen or Cl.

2. The compound of claim 1, wherein $R^1$ is methyl; $R^2$ is Cl or Br; $R^{3b}$ is —$CH_2CH_2N(CH_2CH_3)_2$; $R^5$ is Cl or F; $R^6$ is hydrogen or Cl.

3. The compound of claim 1, wherein $R^1$ is methyl; $R^2$ is Cl; $R^{3b}$ is —$CH_2CH_2N(CH_2CH_3)_2$; $R^5$ is Cl; $R^6$ is hydrogen.

4. An insecticide composition comprising 1 to 99 wt % of the compound of claim 1.

5. A method of controlling a pest in a plant comprising applying to the plant the compound of claim 1 at a concentration of about 0.01 ppm to about 0.5 ppm.

6. The method of claim 5 wherein the pest is *Helicoverpa armigera* or *Ostrinia furnacalis*.

* * * * *